(12) United States Patent
McClellan et al.

(10) Patent No.: US 10,881,803 B2
(45) Date of Patent: Jan. 5, 2021

(54) SYSTEM AND METHOD TO STORE, LOAD AND ADMINISTER A COMPOUND VIA AN AMPULE

(71) Applicants: William T. McClellan, Morgantown, WV (US); Justin Chambers, Morgantown, WV (US)

(72) Inventors: William T. McClellan, Morgantown, WV (US); Justin Chambers, Morgantown, WV (US)

(*) Notice: Subject to any disclaimer, the term of this patent is extended or adjusted under 35 U.S.C. 154(b) by 166 days.

(21) Appl. No.: 15/723,607

(22) Filed: Oct. 3, 2017

(65) Prior Publication Data

US 2018/0093043 A1 Apr. 5, 2018

Related U.S. Application Data

(60) Provisional application No. 62/403,287, filed on Oct. 3, 2016.

(51) Int. Cl.
*A61M 5/24* (2006.01)
*A61M 5/34* (2006.01)
*A61M 5/31* (2006.01)

(52) U.S. Cl.
CPC .......... *A61M 5/2459* (2013.01); *A61M 5/34* (2013.01); *A61M 2005/2492* (2013.01); *A61M 2005/3114* (2013.01); *A61M 2207/00* (2013.01); *A61M 2209/082* (2013.01)

(58) Field of Classification Search
CPC .............. A61M 5/2455; A61M 5/2459; A61M 5/2429; A61M 2005/2485; A61M 2005/2462; A61M 2005/312; A61M 2005/2492; A61M 5/34; A61M 5/2425; A61M 5/285; A61M 5/286
See application file for complete search history.

(56) References Cited

U.S. PATENT DOCUMENTS

| | | | | |
|---|---|---|---|---|
| 5,445,462 | A * | 8/1995 | Johnson | A61M 35/006 401/132 |
| 8,177,063 | B1 * | 5/2012 | Simm | A61M 5/002 206/366 |
| 2013/0012908 | A1 * | 1/2013 | Yeung | A61J 1/1412 604/404 |
| 2013/0204225 | A1 * | 8/2013 | Creaturo | A61M 5/3129 604/506 |
| 2014/0197120 | A1 * | 7/2014 | Seiwell | A61M 5/008 211/85.8 |
| 2016/0279341 | A1 * | 9/2016 | Anderson | A61M 5/3137 |
| 2018/0093045 | A1 * | 4/2018 | Mehawej | A61M 5/2033 |

* cited by examiner

*Primary Examiner* — Bhisma Mehta
*Assistant Examiner* — James D Ponton
(74) *Attorney, Agent, or Firm* — Andrew D. Wright; Roberts Calderon Safran & Cole, P.C.

(57) ABSTRACT

A system includes: a body including an internal cavity and an internal reservoir; a holder configured to hold an ampule and configured to be slidably received in the cavity; and a clip configured to connect to the holder, wherein the holder is configured to slide into the cavity to a first position when the clip is operatively connected to the holder, and wherein the holder is configured to slide into the cavity to a second position when the clip is not connected to the holder. A method includes manufacturing the system. Another method includes administering an injection using the system.

13 Claims, 5 Drawing Sheets

SYSTEM AND METHOD TO STORE, LOAD AND ADMINISTER A COMPOUND VIA AN AMPULE

CROSS REFERENCE TO RELATED APPLICATION

This application claims priority to U.S. Provisional Application No. 62/403,287, filed Oct. 3, 2016, the entire contents of which are incorporated by reference herein.

BACKGROUND

The invention generally relates to medical devices and associated methods of manufacture and use, and more particularly to injectors.

Breaking an ampule by hand and drawing the drug into the syringe can be tedious and cumbersome. In the event of a life or death situation this task can become extremely difficult and could result in the drug being spilled, needle being dropped, damage, etc.

SUMMARY

In a first aspect of the invention there is a system comprising: a body comprising an internal cavity and an internal reservoir; a holder configured to hold an ampule and configured to be slidably received in the cavity; and a clip configured to connect to the holder, wherein the holder is configured to slide into the cavity to a first position when the clip is operatively connected to the holder, and wherein the holder is configured to slide into the cavity to a second position when the clip is not connected to the holder. An aspect of the invention includes a method comprising manufacturing the system. Another aspect of the invention includes a method comprising administering an injection using the system.

In embodiments, the clip, when operatively connected to the holder, prevents the holder from sliding from the first position to the second position.

In aspects, the holder, the internal cavity, and the reservoir are sized and shaped relative to the ampule such that the ampoule does not contact an inclined wall of the reservoir when the holder is in the first position, and the ampule contacts the inclined wall of the reservoir when the holder is in the second position.

In embodiments, the device is configured to break the ampule when the holder is moved from the first position to the second position. Fluid contained in the ampule is contained in the reservoir after the ampule is broken. The system may further comprise a receiver connected to the body, wherein the receiver is in fluidic communication with the reservoir. The receiver may inhibit fluid from escaping the reservoir and may be configured to accept an end of a syringe for extracting the fluid from the reservoir. The receiver may be at a first end of the body and the holder may slide into a second end of the body opposite the first end of the body.

In aspects, the body comprises a syringe holder configured to hold a syringe by friction fit. The system may further comprise a syringe configured to be removably held in the syringe holder. The body may comprise a needle holder configured to hold a needle (or needle sheath containing a needle) by friction fit. The system may further comprise a needle (or needle sheath containing a needle) configured to be removably held in the needle holder, wherein the syringe is configured to be connected to the needle for administering a subcutaneous injection or an intramuscular injection of fluid that was extracted from the reservoir and held in the syringe. The body, the syringe holder, and the needle holder may be integrally formed. The body, the syringe holder, and the needle holder may be 3D printed as a first element, the holder may be 3D printed as a second element, and the clip may be 3D printed as a third element. The body, the syringe holder, and the needle holder may be molded plastic.

In another aspect of the invention there is a method comprising: moving a holder from a first position to a second position within a body, wherein the moving from the first position to the second position causes an ampule held in the holder to break and release fluid into a reservoir within the body; contacting a syringe to a receiver connected to the body; extracting a portion of the fluid from the reservoir into the syringe while the syringe is contacting the receiver; connecting the syringe to a needle; and administering an injection of the portion of the fluid using the connected syringe and needle. In embodiments, the ampule is broken by coming into contact with an inclined wall inside the body. The method may further comprise removing a safety clip from the holder prior to the moving, wherein the safety clip prevents the moving when the safety clip is operatively connected to the holder.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

A device (e.g., a system) according to aspects of the invention is used to store, load and administer a compound easily and safety. The device utilizes an ampule, syringe and needle. The device safely stores the ampule, needle and syringe for transportation. When needed, the syringe can be removed and placed within the receiver at the bottom of the device. The device then breaks the ampule inside allowing the compound to easily and safely be drawn into the syringe. Once the compound is loaded, the syringe can be transferred to the needle and ready for administration.

The device (e.g., the system) according to aspects of the invention safely houses (e.g., stores) an ampule, a syringe, and a needle for handling and/or transportation. When needed, the safety mechanism (safety clip) can be removed. This safety features allows the device to be transported and handled without the risk of premature activation. Once the safety mechanism is removed the device is ready to be activated. The button or slide mechanism can then be pressed or activated allowing the ampule to be broken inside of the cavity. The breaking of the ampule allows the compound to fill the internal reservoir.

Figure 1:
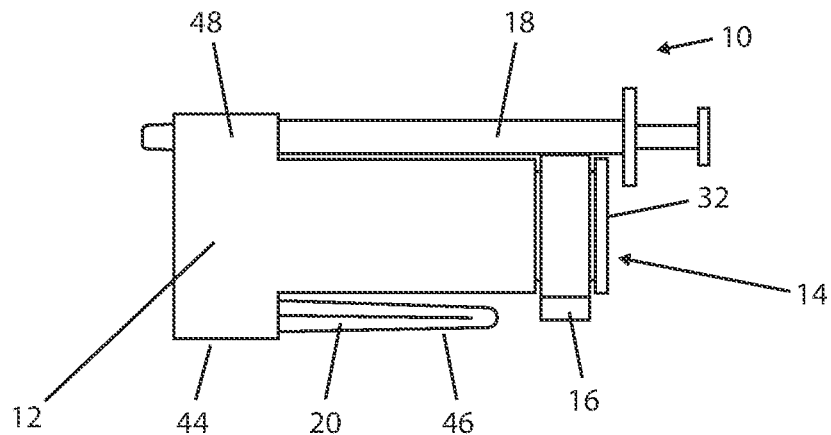
FIG. 1 shows a system in accordance with aspects of the invention.

FIG. 1 shows a system 10 in accordance with aspects of the invention. In embodiments, the system 10 includes a body 12, a holder 14, and a clip 16, the operation of which is described in detail herein. The body 12 may be configured to detachable hold at least one of a syringe 18 and a needle 20.

Figure 2:
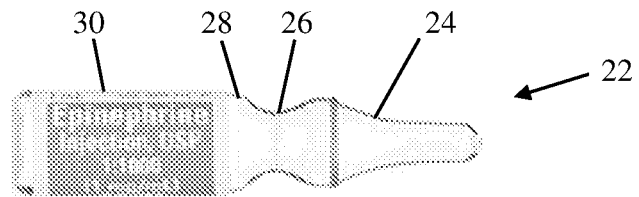
FIG. 2 shows an exemplary ampule that can be used with the system in accordance with aspects of the invention.

FIG. 2 shows an exemplary ampule 22 that can be used with the system 10 in accordance with aspects of the invention. The ampule 22 may be a conventional ampule that stores a dose of a compound, e.g., a fluid to be administered to a person or other animal via injection. For example, the ampule 22 may be a glass ampule that contains a 1 mL volume of a liquid compound that contains 1 mg/mL of epinephrine. The invention is not limited to use with epinephrine, and instead the ampule 22 may contain any desired compound. The invention is not limited to a 1 mL ampule, and instead the system 10 may be structured an arranged to accommodate any desired size ampule containing any desired volume of compound.

As shown in FIG. 2, the ampule 22 includes a head 24, ampule neck 26, shoulder 28, and body 30. As is understood in the art, the ampule neck 26 may be scored or made of relatively thin glass (compared to the head 24 and the shoulder 28), such that the ampule neck 26 is configured to be broken to permit access to the compound contained within the body 30. In conventional use, a user grasps the ampule 22 with two hands, one hand holding the head 24 and another hand holding the body 30 and/or shoulder 28. Using this two-handed grip, the user exerts a bending force on the ampule neck 26 until the glass at the ampule neck 26 breaks. Once the ampule neck 26 has been broken, the head 24 is set aside, and the user may access the compound contained in the body 30.

Figure 3:
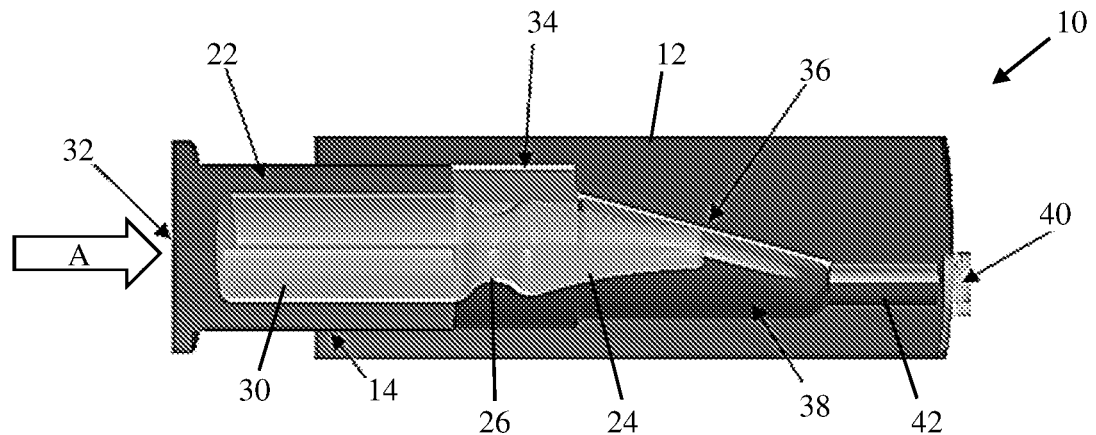
FIG. 3 shows details of an interior of the system in accordance with aspects of the invention.
Figure 8:
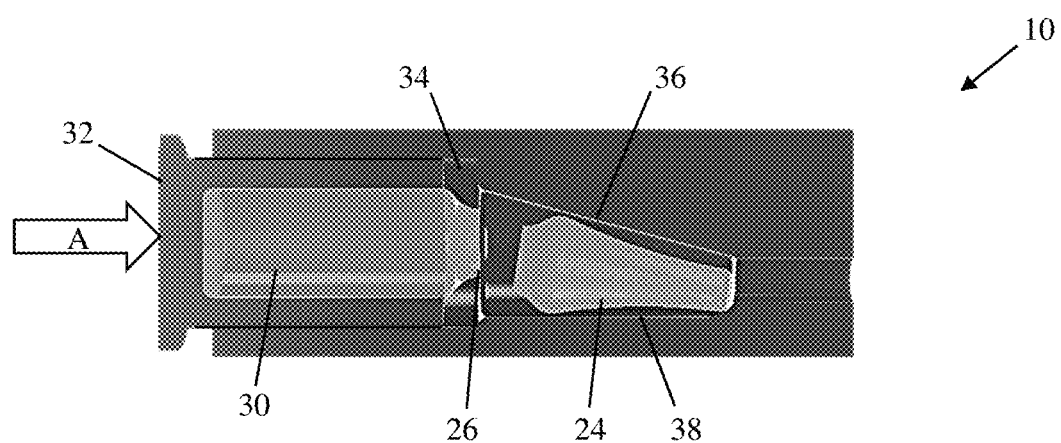
FIG. 8 shows details of an interior of the system in accordance with aspects of the invention.

FIG. 3 shows details of an interior of the system 10 in accordance with aspects of the invention. In the assembled state shown in FIG. 3, the ampule 22 is placed and held within the holder 14. For example, the body 30 of the ampule 22 may be held in a cavity in the holder 14. The holder 14 may include a button 32 to be pressed for activation, which slides within a cavity 34 in the body 12 thereby making the ampule head 24 approach (e.g., move toward) a wedge/incline 36 within the body 12. As shown in FIG. 3, with the clip 16 removed from the device, the holder 14 may be moved in the direction indicated by arrow "A" from a first position to a second position. A number of methods can be used to create the ampule holder 14 and slide mechanism, and the one shown represents a preferred embodiment. As the ampule 22 slides within the cavity 34 of the body 12, from the first position to the second position, the ampule head 24 contacts the wedge/incline 36, which creates a bending moment at the ampule neck 26. This bending moment causes the ampule 22 to break at the ampule neck 26 (as illustrated in FIG. 8) as intended by the ampule manufacturer. Once the ampule 22 is broken, the compound will flow out of the ampule 22 into the reservoir 38 of the body 12. Shaking the body 12 may be applied to assist with the transfer of compound from the ampule 22 into the reservoir 38.

FIG. 3 shows the holder 14 at a first position relative to the cavity 34 of the body 12. FIG. 8 shows the holder 14 at a second position relative to the cavity 34 of the body 12. In operation, the holder 14 is moved from the first position (FIG. 3) to the second position (FIG. 8) by pressing the button 32 in the direction indicated by arrow A. As shown in FIG. 1, the clip 16 is configured to be placed on the holder 14 in a manner that prohibits the holder 14 from moving from the first position to the second position. Removing the clip 16 (as depicted in FIGS. 3 and 8) permits the holder 14 to move relative to the body 12 in the direction of arrow A.

Once the compound is within the reservoir 38, the syringe can be placed within the receiver 40 at the bottom of the body 12 to withdraw the compound into the syringe from the reservoir 38. A passage 42 may be formed in the body 12, whereby the passage 42 provides a fluid communication path between the reservoir 38 and the receiver 40. The syringe can be placed in the receiver at any time. The receiver 40, which connects the syringe to the reservoir 38, can have a breakable seal, valve, etc., to allow the fluid (e.g., the compound) to transfer only when a syringe is inserted into the receiver 40. This allows the device to hold the compound within the reservoir 38 before a syringe in placed in the receiver 40. This receiver 40 can also have a filter to filter the compound before entering the syringe.

Figure 4:
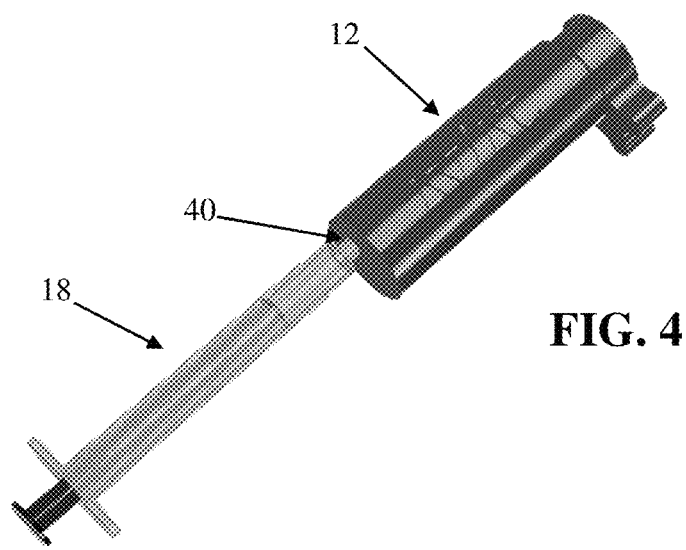
FIG. 4 depicts a syringe withdrawing fluid from the system in accordance with aspects of the invention.
Figures 5, 6:
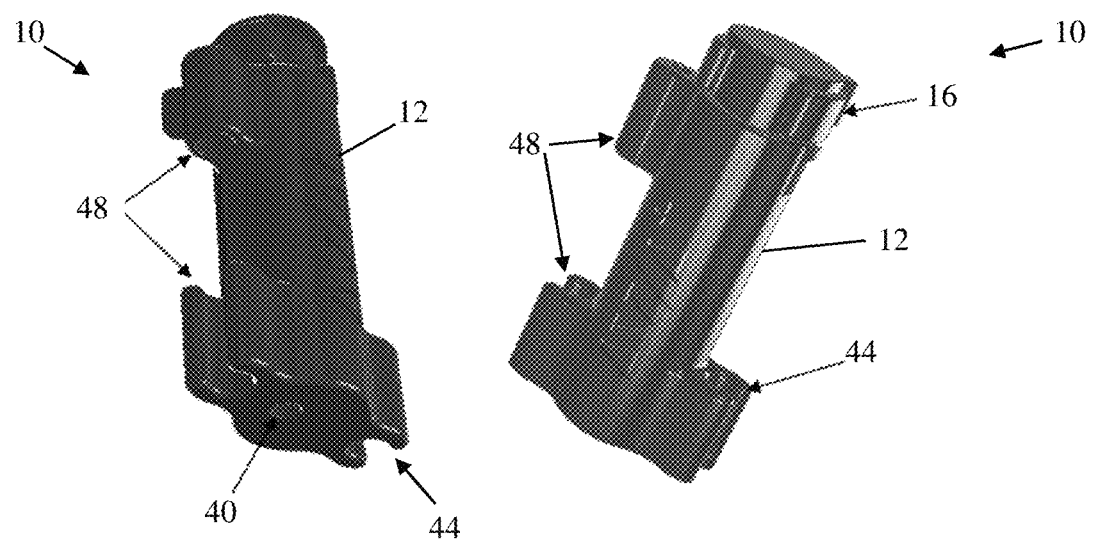
FIGS. 5 and 6 show additional views of the system in accordance with aspects of the invention.

The syringe, which is selectively secured to the body 12, can be removed from its holder and transferred to the receiver 40 where it can withdraw the compound from the reservoir 38 to the desired level. This is illustrated in FIGS. 4 and 7B, which show a syringe 18 connected to the receiver 40 for withdrawing fluid from the reservoir 38 into the syringe 18. The compound can be withdrawn, measured, manipulated to removable of air bubbles, etc., all while it is within the receiver 38 if needed. As illustrated in FIG. 7C, once the desired measure of compound is achieved, the syringe 18 can be transferred to the needle 20 that is held within a needle holder 44. As illustrated in FIG. 7D, the syringe 18 is transferred to the needle 20 and used to withdraw the needle 20 from a protective sheath 46, and the syringe 18 is now ready for administration (e.g., with the needle 20 connected to the syringe 18).

After administration the needle 20 to can be placed back into the needle sheath 46 which is held secure by the device, e.g., by the needle holder 44 of the body 12. The syringe 18 can be placed back into its holder 48 and the broken ampule remains contained within the device. This provides a safe method to handle, transport and dispose of the device and contents after use.

The inventive device (e.g., the system 10) can be manufactured by any number of methods. It can also utilize new additive manufacturing techniques such as 3D printing. The device can be disposable or reusable and tailored to a specific application or user. The device can be manufactured with a variety of materials based on the needs of the end user with the preferred embodiment being constructed out of plastic material.

Figure 7A:
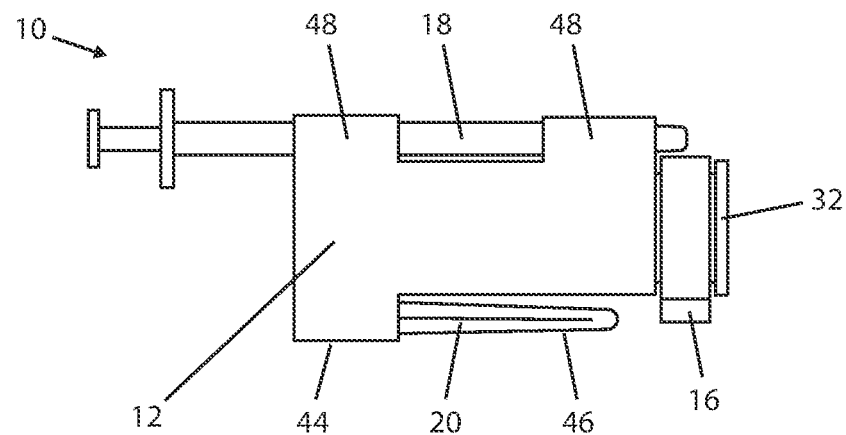
FIGS. 7A-D depict a sequence of using the system in accordance with aspects of the invention.
Figure 7B:
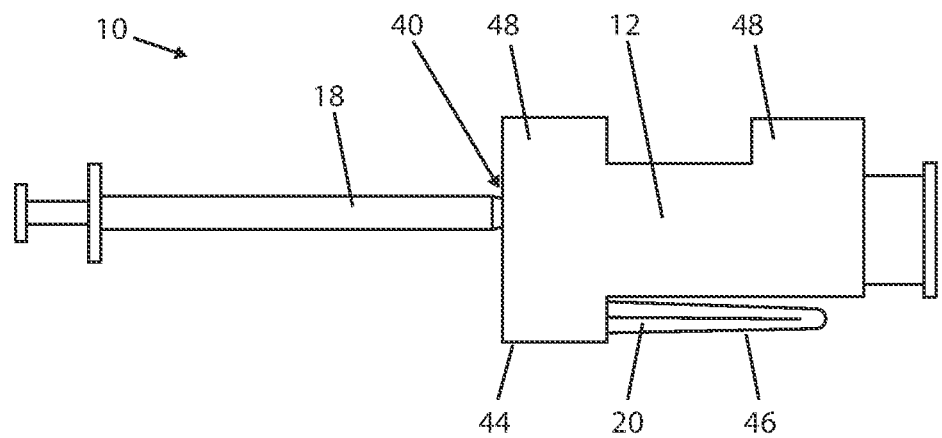
Figure 7C:
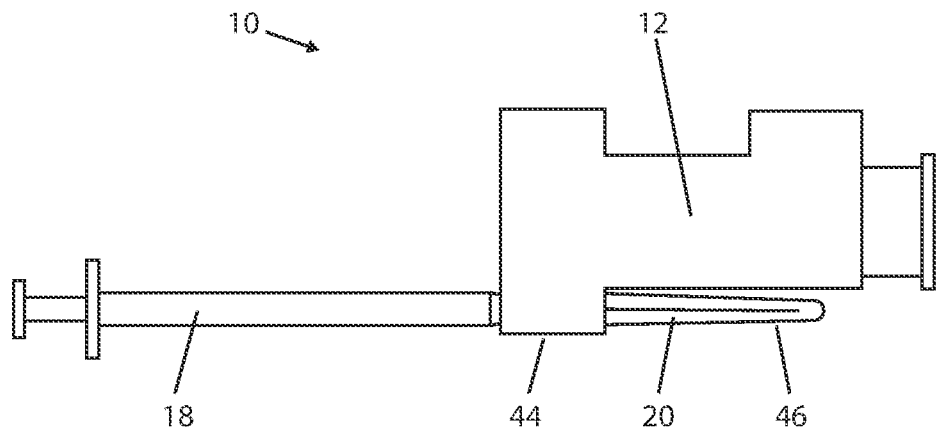
Figure 7D:
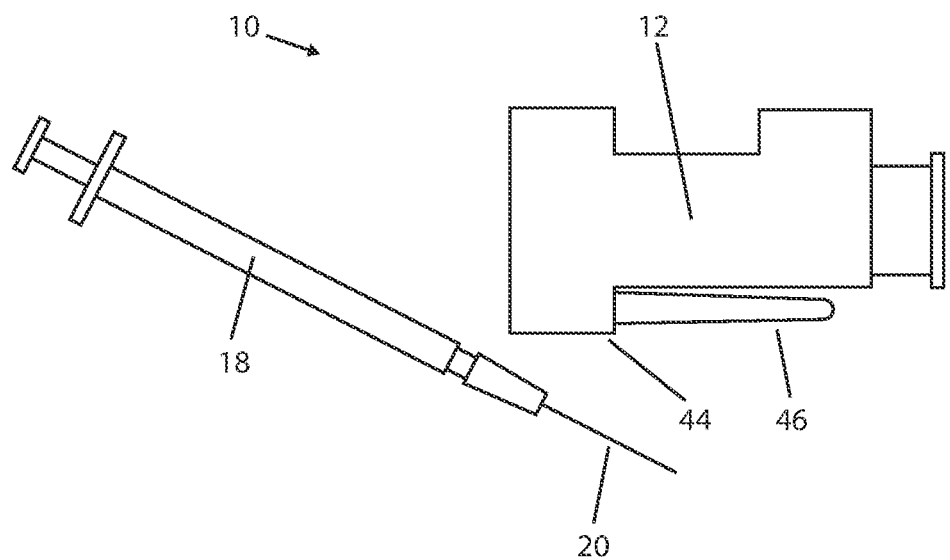

FIGS. 7A-D show a sequence of using the device (e.g., the system 10). FIG. 7A shows the device (e.g., system 10) with the syringe 18 and needle 20 stowed in their respective holders (syringe holder 48 and needle holder 44) on the body 12 of the device. FIG. 7B shows the syringe 18 contacting the receiver 40 for withdrawing compound from the reservoir 38. FIG. 7C shows the syringe 18 connecting to the needle 20 while the needle 20 is stowed in its holder 44. FIG. 7D shows the syringe 18 and needle 20 connected to one another and disengaged from the body 12 of the device such that the syringe 18 and needle 20 and ready to inject.

An aspect of the invention includes the device, e.g., the system 10. Another aspect of the invention includes the device, e.g., the system 10, with the syringe 18 and needle 20. Another aspect of the invention includes a method of using the device, e.g., the system 10. Another aspect of the invention includes a method of manufacturing the device, e.g., the system 10.

Once the syringe 18 is loaded with fluid from the reservoir 38 (fluid that was originally in the ampule 22), the syringe 18 can be connected to the needle 20, and the connected syringe 18 and needle 20 can be used to administer an injection of the fluid to an individual (e.g., a subcutaneous injection or an intramuscular injection). Any type of injectable fluid may be used with implementations of the invention, including but not limited to epinephrine.

As shown in FIG. 1, the syringe holder 48 may comprise a single holding portion connected to (or integrally formed with) the exterior of the body 12. Alternatively, as shown in FIGS. 5, 6, and 7A-D, the syringe holder 48 may comprise more than one (e.g., two) holding portions arranged at opposite ends of the body 12. In both alternatives, aside from the different design of the syringe holder, the remainder of the system 10 operates in the manner described herein.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A system, comprising:
   a body comprising an internal cavity and an internal reservoir;
   a holder configured to hold an ampule and configured to be slidably received in the cavity; and
   a clip configured to connect to the holder, wherein the holder is configured to slide into the cavity to a first position when the clip is operatively connected to the holder, and wherein the holder is configured to slide into the cavity to a second position when the clip is not connected to the holder,
   wherein the clip, when operatively connected to the holder, prevents the holder from sliding from the first position to the second position;
   wherein the holder, the internal cavity, and the reservoir are sized and shaped relative to the ampule such that the ampule does not contact an inclined wall of the reservoir when the holder is in the first position, and the ampule contacts the inclined wall of the reservoir when the holder is in the second position;
   wherein the system is configured to break the ampule when the holder is moved from the first position to the second position;
   wherein fluid contained in the ampule is contained in the reservoir after the ampule is broken;
   further comprising a receiver connected to the body, wherein the receiver is in fluidic communication with the reservoir;
   wherein the receiver inhibits fluid from escaping the reservoir and is configured to accept an end of a syringe for extracting the fluid from the reservoir;
   wherein the body comprises a syringe holder configured to hold the syringe by friction fit;
   wherein the body comprises a needle holder configured to hold a needle sheath containing a needle by friction fit;
   wherein the body, the syringe holder, and the needle holder are integrally formed;
   wherein the syringe holder comprises: a first holding portion protruding from the body at a first end of the body; a second holding portion protruding from the body at a second end of the body opposite the first end of the body; and an open space between the first holding portion and the second holding portion;
   wherein the first holding portion and the second holding portion are on a first side of the body; and
   wherein the needle holder comprises a third holding portion protruding from a second side of the body opposite the first side of the body.

2. The system of claim 1, further comprising a syringe configured to be removably held in the syringe holder.

3. The system of claim 2, further comprising a needle or a needle sheath containing a needle configured to be removably held in the needle holder, wherein the syringe is configured to be connected to the needle for administering a subcutaneous injection or an intramuscular injection of fluid that was extracted from the reservoir and held in the syringe.

4. The system of claim 1, wherein the body, the syringe holder, and the needle holder are 3D printed as a first element, the holder is 3D printed as a second element, and the clip is 3D printed as a third element.

5. The system of claim 1, wherein the body, the syringe holder, and the needle holder are molded plastic.

6. The system of claim 1, wherein the receiver has a breakable seal that allows the fluid to transfer through the receiver only when the syringe is inserted into the receiver.

7. The system of claim 1, wherein the receiver has a valve that allows the fluid to transfer through the receiver only when the syringe is inserted into the receiver.

8. The system of claim 1, further comprising a passage inside the body, the passage extending between the reservoir and the receiver.

9. A method comprising manufacturing the system of claim 1.

10. A method comprising administering an injection using the system of claim 1.

11. A system, comprising:
    a body comprising an internal cavity and an internal reservoir;
    a holder configured to hold an ampule and configured to be slidably received in the cavity; and
    a clip configured to connect to the holder, wherein the holder is configured to slide into the cavity to a first position when the clip is operatively connected to the holder, and wherein the holder is configured to slide into the cavity to a second position when the clip is not connected to the holder, wherein the holder comprises a first end, a second end, a central portion between the first end and the second end, and a button at the first end;

wherein the button has a larger diameter than the central portion;

wherein the clip, when operatively connected to the holder, fits around the central portion and is between the button and the body;

wherein the clip, when operatively connected to the holder, prevents the holder from sliding from the first position to the second position;

wherein the holder, the internal cavity, and the reservoir are sized and shaped relative to the ampule such that the ampule does not contact an inclined wall of the reservoir when the holder is in the first position, and the ampule contacts the inclined wall of the reservoir when the holder is in the second position; and wherein the system is configured to break the ampule when the holder is moved from the first position to the second position.

12. The system of claim 4, wherein the body comprises a syringe holder configured to hold a syringe by friction fit, the syringe holder being on a first side of the body;

wherein the body comprises a needle holder configured to hold a needle sheath containing a needle by friction fit, the needle holder being on a second side of the body opposite the first side of the body; and wherein the body, the syringe holder, and the needle holder are integrally formed.

13. The system of claim 12, wherein the syringe holder comprises: a first holding portion protruding from the body at a first end of the body; a second holding portion protruding from the body at a second end of the body opposite the first end of the body; and an open space between the first holding portion and the second holding portion; and wherein the needle holder comprises a third holding portion protruding from the body at the first end of the body.

* * * * *